United States Patent
Sokulin et al.

(10) Patent No.: US 12,318,245 B2
(45) Date of Patent: Jun. 3, 2025

(54) METHODS AND SYSTEMS FOR IMAGING A NEEDLE FROM ULTRASOUND IMAGING DATA

(71) Applicant: GE Precision Healthcare LLC, Milwaukee, WI (US)

(72) Inventors: Alexander Sokulin, Kiryat Tivon (IL); Cynthia Owen, Powhatan, AR (US); Menachem Halmann, Monona, WI (US); Dani Pinkovich, Haifa (IL)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 534 days.

(21) Appl. No.: 16/512,202

(22) Filed: Jul. 15, 2019

(65) Prior Publication Data

US 2021/0015448 A1 Jan. 21, 2021

(51) Int. Cl.
*A61B 8/08* (2006.01)
*A61B 8/00* (2006.01)
*A61B 34/10* (2016.01)
*A61B 34/20* (2016.01)

(52) U.S. Cl.
CPC ........... *A61B 8/0841* (2013.01); *A61B 34/20* (2016.02); *A61B 8/5215* (2013.01); *A61B 2034/107* (2016.02); *A61B 2034/2063* (2016.02)

(58) Field of Classification Search
USPC ........................................................ 600/424
See application file for complete search history.

(56) References Cited

U.S. PATENT DOCUMENTS

| | | | | |
|---|---|---|---|---|
| 6,077,226 A | * | 6/2000 | Washburn | A61B 8/461 600/443 |
| 6,951,542 B2 | | 10/2005 | Greppi et al. | |
| 8,852,111 B2 | | 10/2014 | Park et al. | |
| 9,398,895 B2 | | 7/2016 | Lin et al. | |
| 2004/0002653 A1 | * | 1/2004 | Greppi | A61B 10/0233 600/439 |
| 2007/0167762 A1 | * | 7/2007 | Kim | A61B 8/0833 600/437 |
| 2012/0179038 A1 | * | 7/2012 | Meurer | A61B 8/463 600/443 |
| 2014/0187942 A1 | * | 7/2014 | Wang | A61B 8/0841 600/439 |
| 2014/0350390 A1 | * | 11/2014 | Kudavelly | A61B 10/0233 600/424 |

(Continued)

FOREIGN PATENT DOCUMENTS

| | | | | |
|---|---|---|---|---|
| CN | 106361369 A | * | 2/2017 | |
| WO | WO-2018145244 A1 | * | 8/2018 | A61B 8/00 |
| WO | WO-2019205167 A1 | * | 10/2019 | A61B 8/085 |

OTHER PUBLICATIONS

CN-106361369-A machine translation (Year: 2017).*

(Continued)

*Primary Examiner* — Jason M Ip
*Assistant Examiner* — Renee C Langhals
(74) *Attorney, Agent, or Firm* — McCoy Russell LLP

(57) ABSTRACT

Various methods and systems are provided for imaging a needle using an ultrasound imager. In one example, a method may include receiving a target path or a target area of a needle, and adjusting a steering angle of an ultrasound beam emitted from an ultrasound probe based on the target path or the target area.

18 Claims, 7 Drawing Sheets

(56) References Cited

U.S. PATENT DOCUMENTS

| | | | |
|---|---|---|---|
| 2016/0081666 A1* | 3/2016 | Deguchi | A61B 8/0841 |
| | | | 600/424 |
| 2016/0183913 A1* | 6/2016 | Singh | G06K 9/6269 |
| | | | 600/459 |
| 2016/0199023 A1* | 7/2016 | Pelissier | A61B 8/4254 |
| | | | 600/424 |
| 2016/0317118 A1 | 11/2016 | Parthasarathy et al. | |
| 2016/0374643 A1 | 12/2016 | Halmann et al. | |
| 2016/0374644 A1* | 12/2016 | Mauldin, Jr. | A61B 8/085 |
| | | | 600/424 |
| 2017/0020559 A1 | 1/2017 | Srinivasan et al. | |
| 2018/0168537 A1* | 6/2018 | Hsieh | A61B 8/5215 |
| 2018/0263593 A1 | 9/2018 | Dickie et al. | |
| 2019/0015160 A1* | 1/2019 | Maeda | A61B 6/032 |
| 2019/0200951 A1* | 7/2019 | Meier | A61B 8/54 |
| 2019/0378293 A1* | 12/2019 | Mwikirize | A61B 5/7267 |
| 2021/0100626 A1* | 4/2021 | St. Pierre | G16H 30/40 |
| 2021/0212658 A1* | 7/2021 | McGrath | A61B 34/25 |

OTHER PUBLICATIONS

WO-2018145244-A1—machine translation (Year: 2018).*
WO-2019205167-A1—machine translation (Year: 2019).*
International Application No. PCT/US2020/039558 filed Jun. 25, 2020—International Search Report and Written Opinion issued on Sep. 29, 2020; 12 pages.

* cited by examiner

METHODS AND SYSTEMS FOR IMAGING A NEEDLE FROM ULTRASOUND IMAGING DATA

FIELD

Embodiments of the subject matter disclosed herein relate to medical imaging, such as ultrasound imaging, and more particularly to displaying images including needles from ultrasound imaging data.

BACKGROUND

Medical imaging systems are often used to monitor and image a subject. In some examples, the medical imaging system may be an ultrasound system used to detect a presence of a needle, such as a biopsy needle, inserted in the subject. In this way, the ultrasound system may be employed to locate and track the needle in the subject during a medical procedure.

One or more images obtained with the ultrasound system may be presented to a user at a user interface. The user may be a medical professional familiar with the medical procedure, and thus the user may have a general impression of where the needle is in the subject, a type of tissue the needle is inserted in, a depth of the needle in the subject, a total length of the needle, etc. However, the user may be unfamiliar with mechanical details of an ultrasound probe of the ultrasound system, such as a steering angle of an ultrasound beam emitted by the ultrasound probe.

BRIEF DESCRIPTION

In one embodiment, a method may include receiving a target path or a target area of a needle, and adjusting a steering angle of an ultrasound beam emitted from an ultrasound probe based on the target path or the target area.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
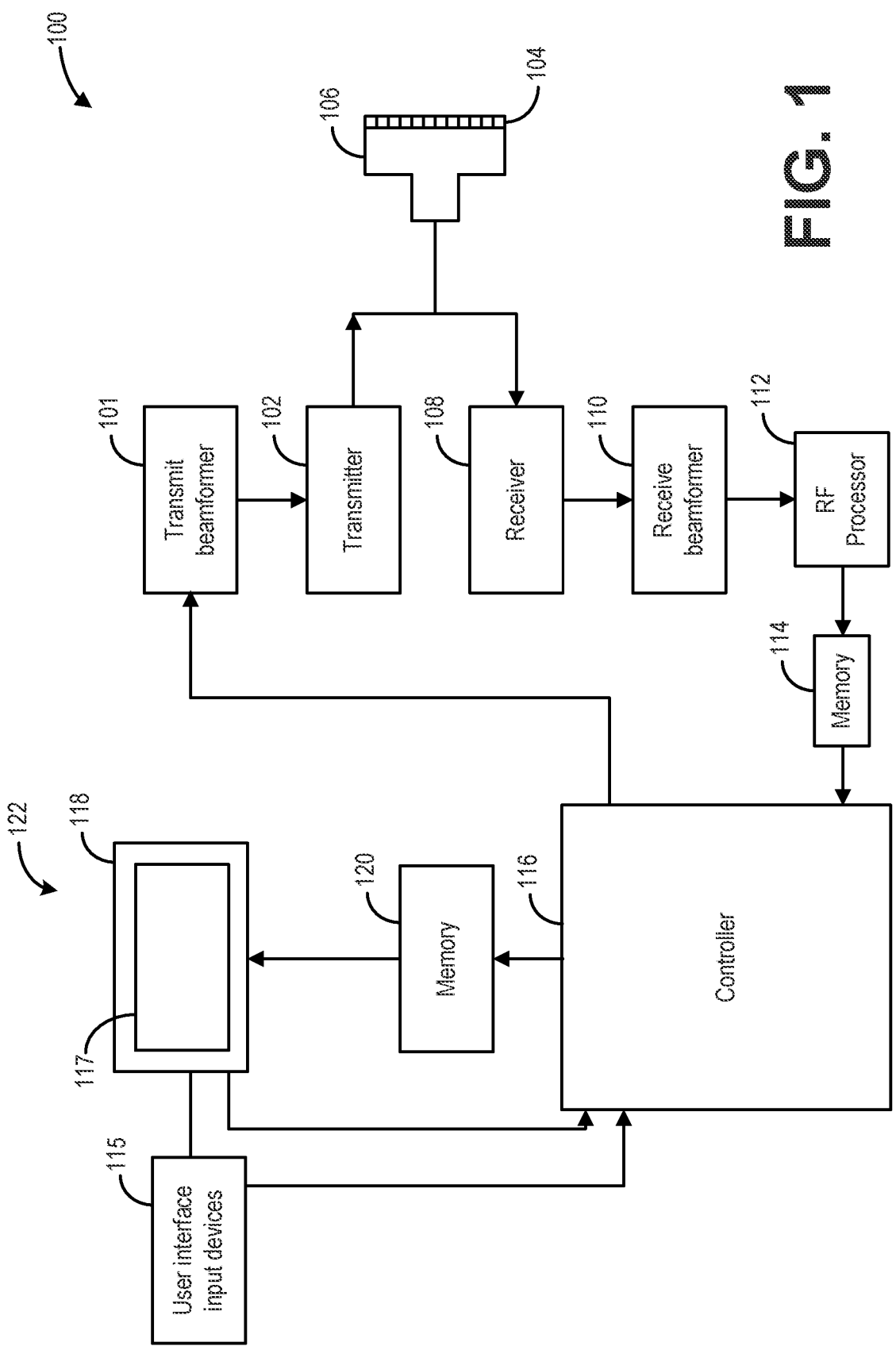
FIG. 1 shows an example ultrasound imaging system according to an exemplary embodiment.
Figure 2:
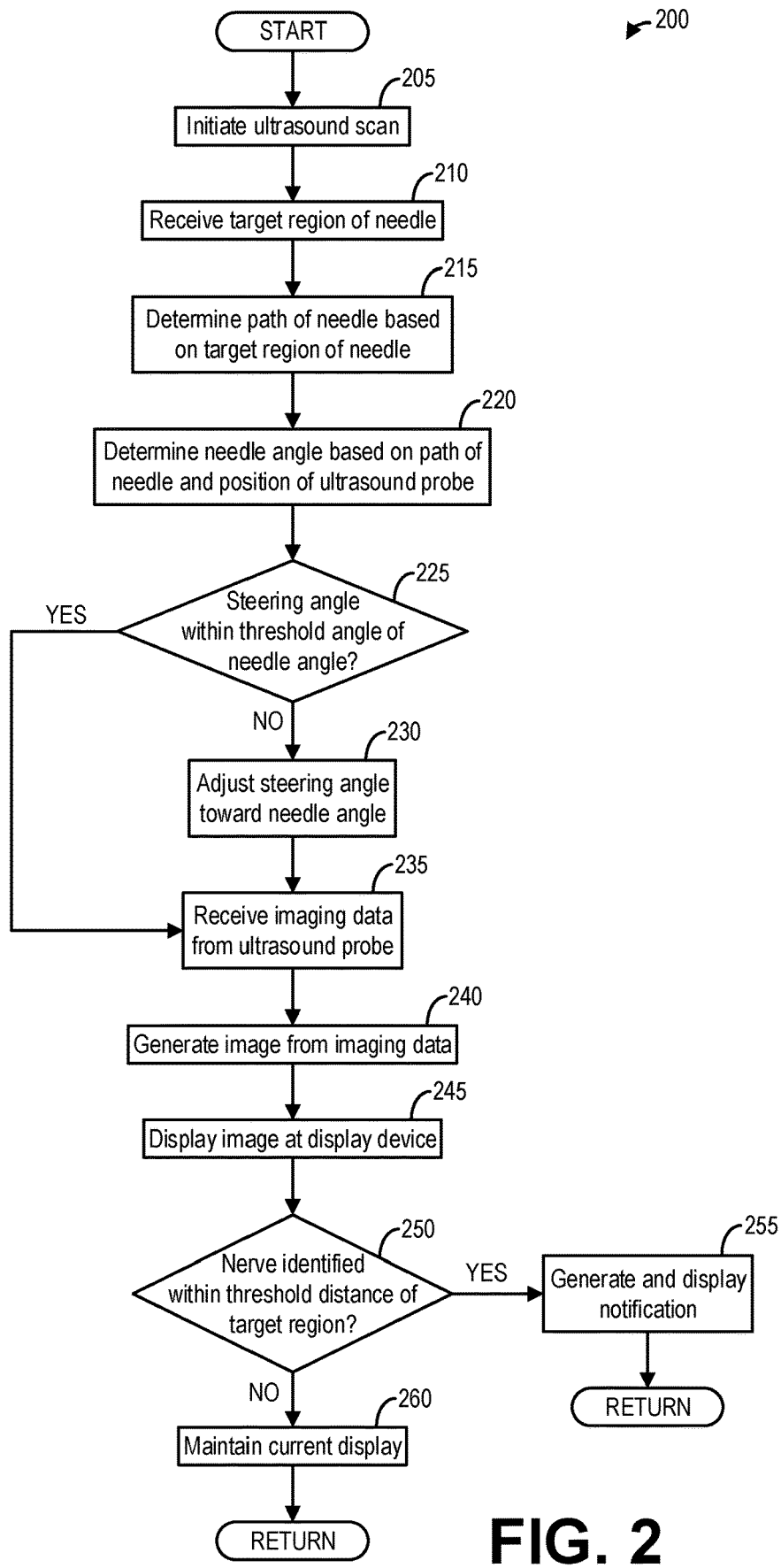
FIG. 2 shows a flow chart of a method for adjusting a steering angle of an ultrasound beam emitted by an ultrasound probe and imaging a needle therefrom, according to an embodiment.
Figure 3:
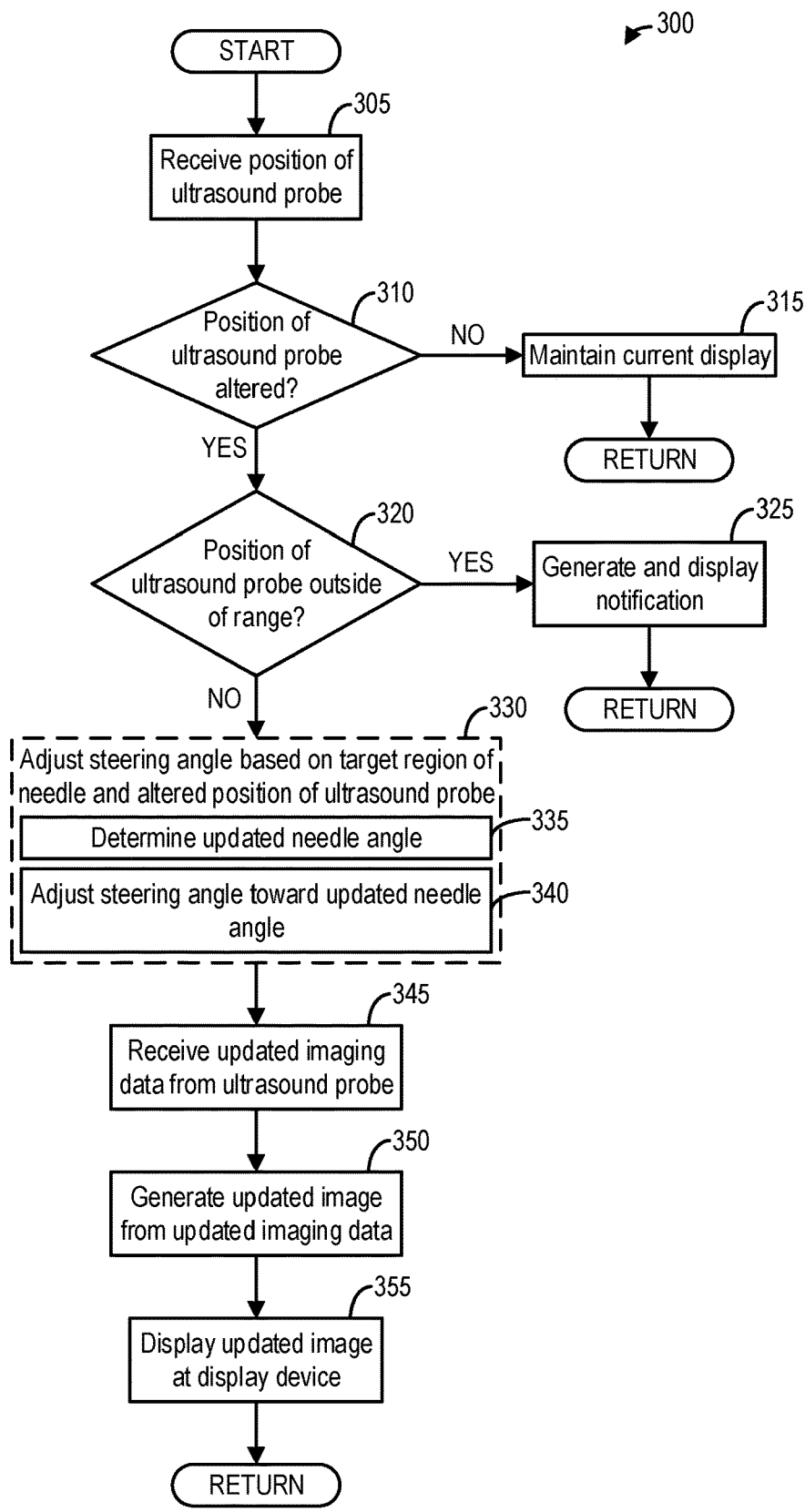
FIG. 3 shows a flow chart of a method for adjusting the steering angle of the ultrasound beam emitted by the ultrasound probe in response to a position of the ultrasound probe being altered and imaging the needle therefrom, according to an embodiment.
Figure 4:
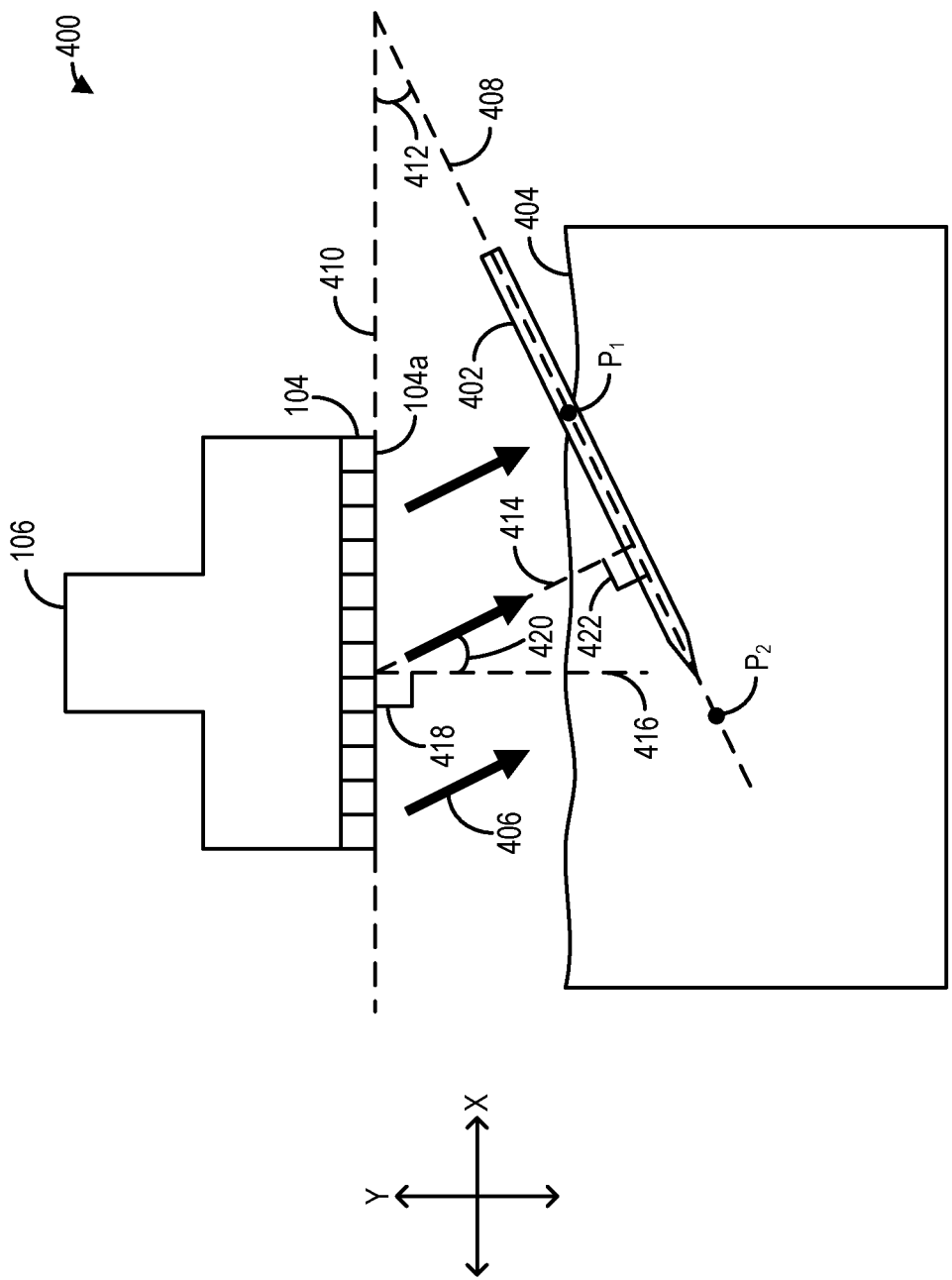
FIG. 4 shows a schematic diagram illustrating geometric considerations of adjusting the steering angle based on an angle between a path of the needle and a surface of the ultrasound probe, according to an embodiment.
Figure 5:
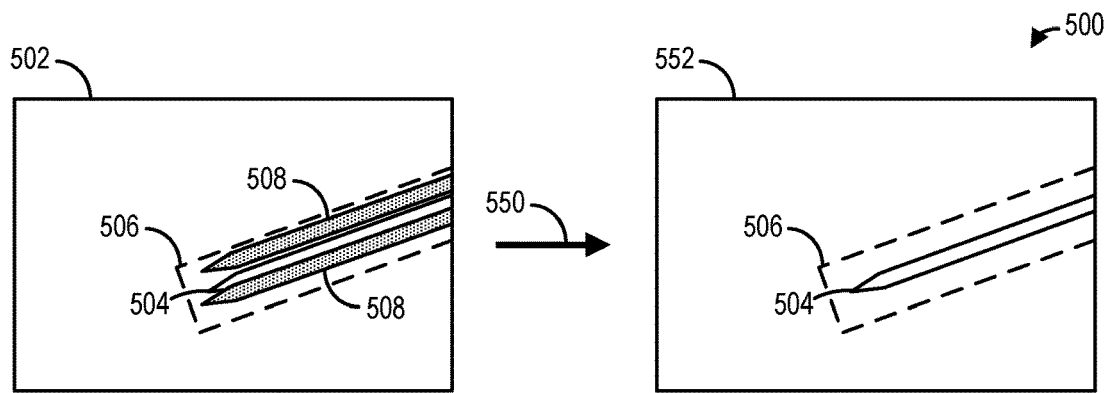
FIG. 5 shows a schematic diagram illustrating a first example of an image transform, according to an embodiment.
Figure 6:
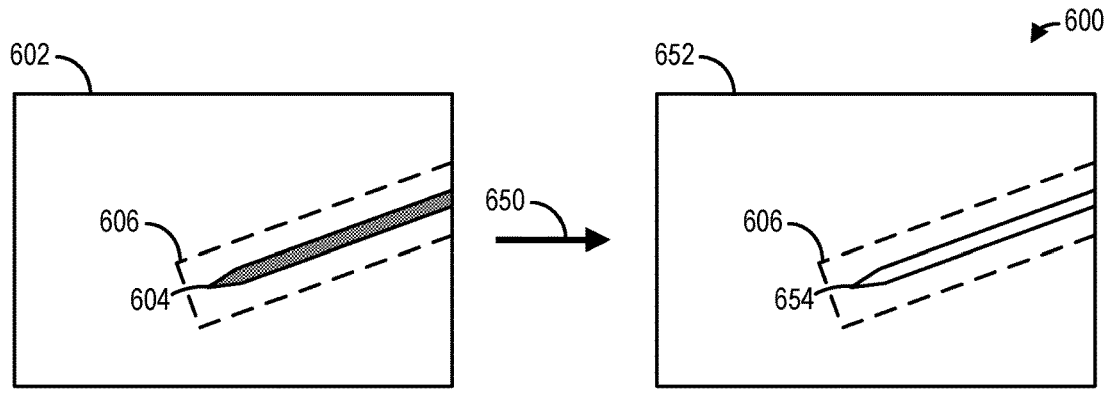
FIG. 6 shows a schematic diagram illustrating a second example of the image transform, according to an embodiment.
Figure 7:
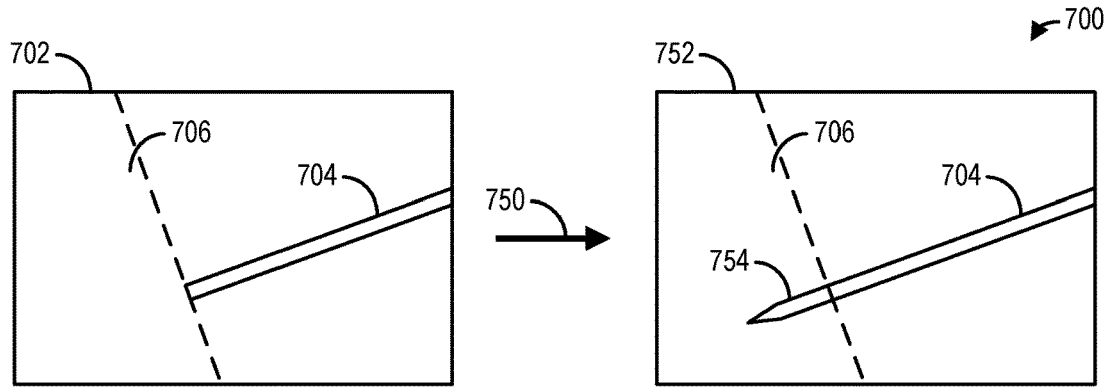
FIG. 7 shows a schematic diagram of an example process for generating a portion of the needle in an image, according to an embodiment.
Figure 8:
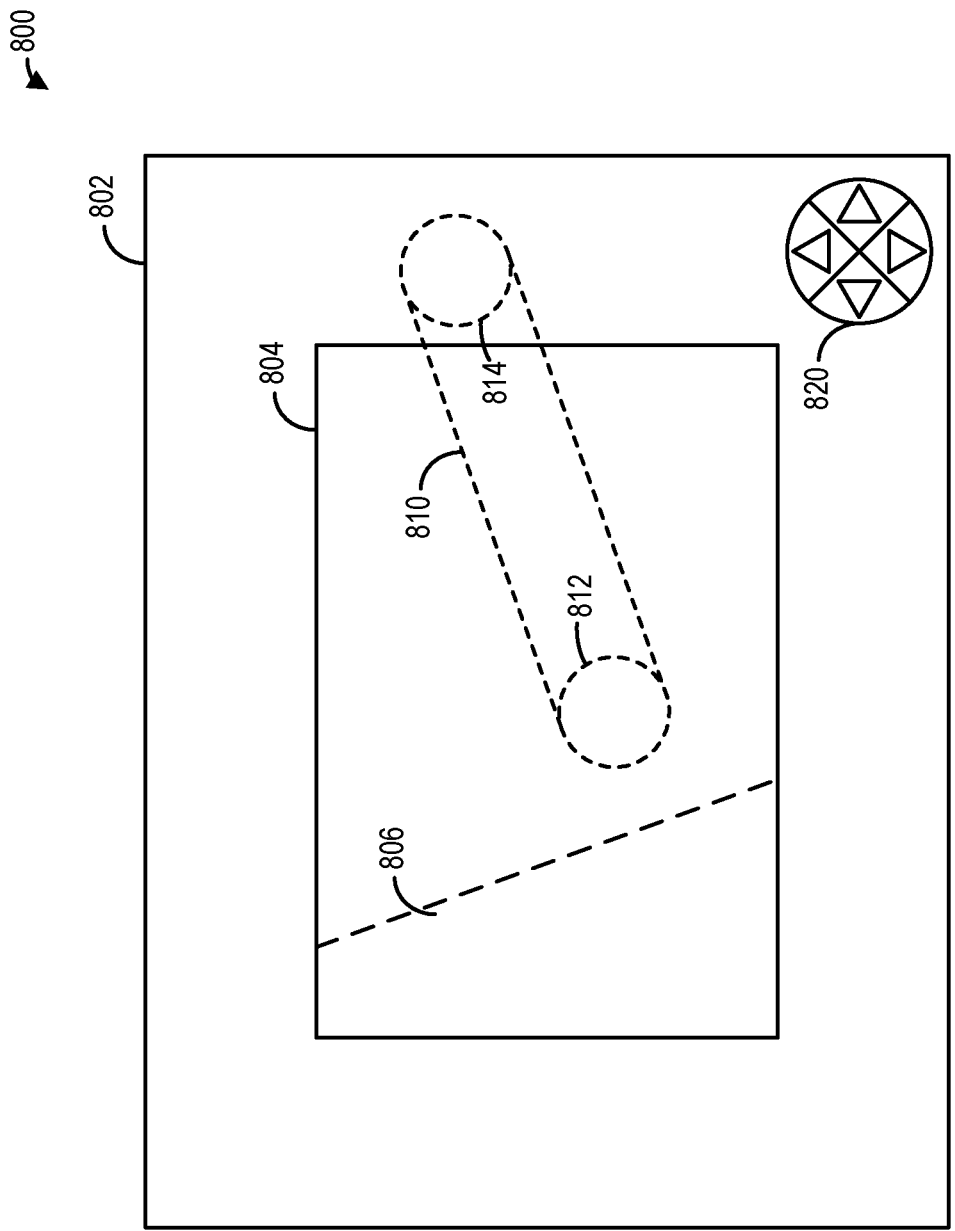
FIG. 8 shows a first example user interface display of a display device of the ultrasound imaging system, according to an embodiment.
Figure 9:
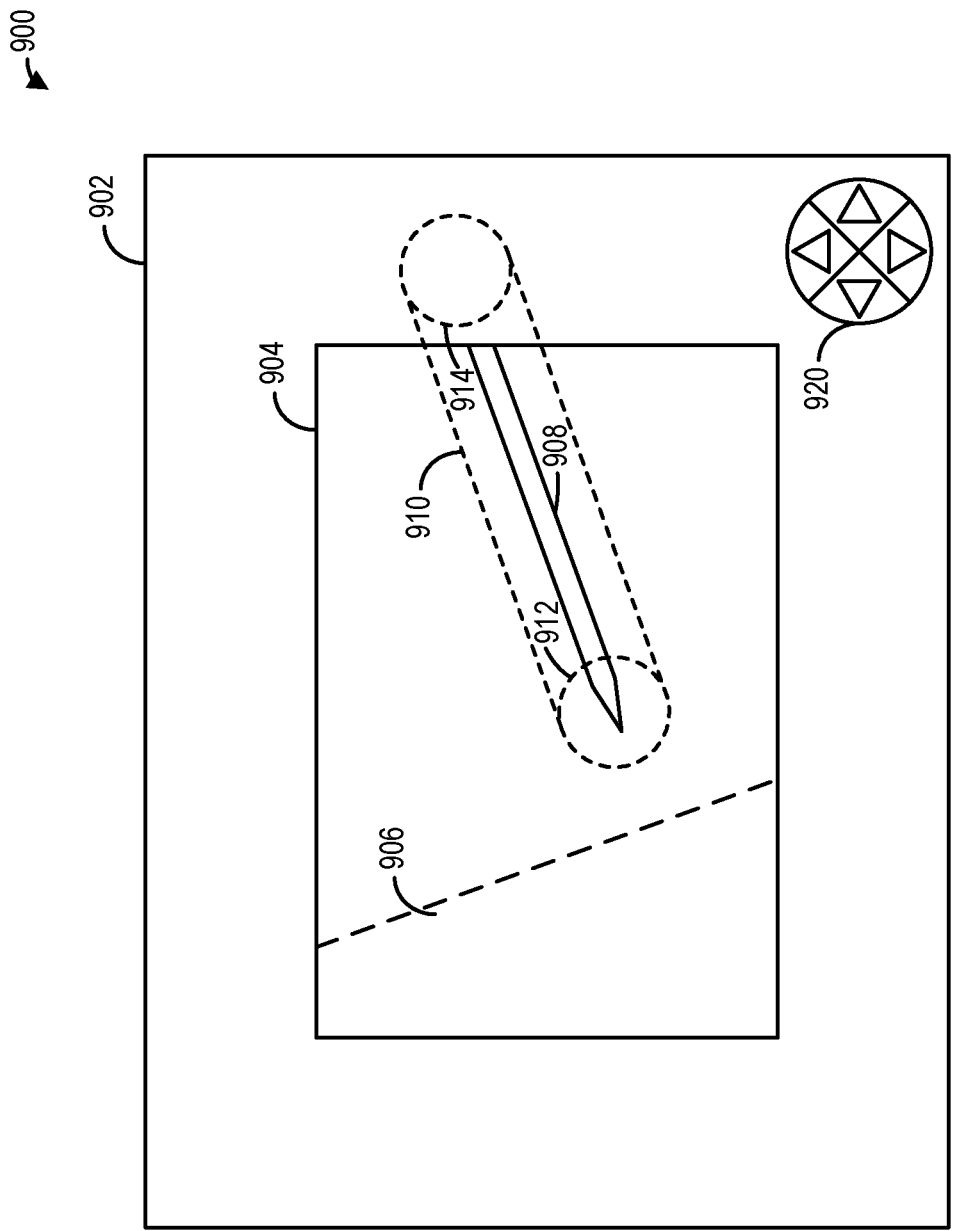
FIG. 9 shows a second example user interface display of the display device of the ultrasound imaging system, according to an embodiment.

The following description relates to various embodiments of adjusting a steering angle of an ultrasound beam emitted by an ultrasound probe and imaging a needle therefrom. One example ultrasound imaging system for generating imaging data therefor is depicted in FIG. 1. FIGS. 2 and 3 depict methods for adjusting the steering angle of the ultrasound beam and imaging the needle therefrom. Geometric considerations of an adjustment of the steering angle are schematically illustrated at FIG. 4. FIGS. 5-7 show example processes of generating an image depicting the needle, such as via an image transform. FIGS. 8 and 9 depict example user interface displays of a display device of the ultrasound imaging system, where the image depicting the needle may be displayed.

FIG. 1 depicts a block diagram of a system 100 according to one embodiment. In the illustrated embodiment, the system 100 is an imaging system and, more specifically, an ultrasound imaging system. However, it is understood that embodiments set forth herein may be implemented using other types of medical imaging modalities (e.g., MR, CT, PET/CT, SPECT etc.). Furthermore, it is understood that other embodiments do not actively acquire medical images. Instead, embodiments may retrieve image or ultrasound data that was previously acquired by an imaging system and analyze the image data as set forth herein. As shown, the system 100 includes multiple components. The components may be coupled to one another to form a single structure, may be separate but located within a common room, or may be remotely located with respect to one another. For example, one or more of the modules described herein may operate in a data server that has a distinct and remote location with respect to other components of the system 100, such as a probe and user interface. Optionally, in the case of ultrasound systems, the system 100 may be a unitary system that is capable of being moved (e.g., portably) from room to room. For example, the system 100 may include wheels or be transported on a cart.

In the illustrated embodiment, the system 100 includes a transmit beamformer 101 and transmitter 102 that drives an array of elements 104, for example, piezoelectric crystals, within a diagnostic ultrasound probe 106 (or transducer) to emit ultrasonic signals (e.g., continuous or pulsed) into a body or volume (not shown) of a subject. The elements 104 and the probe 106 may have a variety of geometries. The ultrasonic signals are back-scattered from structures in a body, for example, an inserted needle, to produce echoes that return to the elements 104. The echoes are received by a receiver 108. The received echoes are provided to a receive beamformer 110 that performs beamforming and outputs a radio frequency (RF) signal. The RF signal is then provided to an RF processor 112 that processes the RF signal. Alternatively, the RF processor 112 may include a complex demodulator (not shown) that demodulates the RF signal to form I/Q data pairs representative of the echo signals. The RF or I/Q signal data may then be provided directly to a memory 114 for storage (for example, temporary storage). The system 100 also includes a system controller 116 that may be part of a single processing unit (e.g., processor) or distributed across multiple processing units. The system controller 116 is configured to control operation of the system 100.

For example, the system controller 116 may include an image-processing module that receives image data (e.g., ultrasound signals in the form of RF signal data or I/Q data pairs) and processes image data. For example, the image-processing module may process the ultrasound signals to generate two-dimensional (2D) slices or frames of ultrasound information (e.g., ultrasound images) or ultrasound waveforms (e.g., continuous or pulse wave Doppler spectrum or waveforms) for displaying to the operator. When the system 100 is an ultrasound system, the image-processing module may be configured to perform one or more processing operations according to a plurality of selectable ultrasound modalities on the acquired ultrasound information. By way of example only, the ultrasound modalities may include color-flow, acoustic radiation force imaging (ARFI), B-mode, A-mode, M-mode, spectral Doppler, acoustic streaming, tissue Doppler module, C-scan, and elastography. Further, in some examples, the one or more processing operations may include one or more image transforms, such as a Radon transform for identifying linear features in the ultrasound images.

Acquired ultrasound information may be processed in real-time during an imaging session (or scanning session) as the echo signals are received. Additionally or alternatively, the ultrasound information may be stored temporarily in the memory 114 during an imaging session and processed in less than real-time in a live or off-line operation. An image memory 120 is included for storing processed slices or waveforms of acquired ultrasound information that are not scheduled to be displayed immediately. The image memory 120 may comprise any known data storage medium, for example, a permanent storage medium, removable storage medium, and the like. Additionally, the image memory 120 may be a non-transitory storage medium.

In operation, an ultrasound system may acquire data, for example, 2D data sets, spectral Doppler data sets, and/or volumetric data sets by various techniques (for example, three-dimensional (3D) scanning, real-time 3D imaging, volume scanning, 2D scanning with probes having positioning sensors, freehand scanning using a voxel correlation technique, scanning using 2D or matrix array probes, and the like). Ultrasound spectrum (e.g., waveforms) and/or images may be generated from the acquired data (at the controller 116) and displayed to the operator or user on the display device 118.

The system controller 116 is operably connected to a user interface 122 that enables an operator to control at least some of the operations of the system 100. The user interface 122 may include hardware, firmware, software, or a combination thereof that enables an individual (e.g., an operator) to directly or indirectly control operation of the system 100 and the various components thereof. As shown, the user interface 122 includes a display device 118 having a display area 117. In some embodiments, the user interface 122 may also include one or more user interface input devices 115, such as a physical keyboard, mouse, and/or touchpad. In one embodiment, a touchpad may be configured to the system controller 116 and display area 117, such that when a user moves a finger/glove/stylus across the face of the touchpad, a cursor atop the ultrasound image or Doppler spectrum on the display device 118 moves in a corresponding manner.

In an exemplary embodiment, the display device 118 is a touch-sensitive display (e.g., touchscreen) that can detect a presence of a touch from the operator on the display area 117 and can also identify a location of the touch in the display area 117. The touch may be applied by, for example, at least one of an individual's hand, glove, stylus, or the like. As such, the touch-sensitive display may also be characterized as an input device that is configured to receive inputs from the operator (such as a request to adjust or update an orientation of a displayed image). The display device 118 also communicates information from the controller 116 to the operator by displaying the information to the operator. The display device 118 and/or the user interface 122 may also communicate audibly. The display device 118 is configured to present information to the operator during or after the imaging or data acquiring session. The information presented may include ultrasound images (e.g., one or more 2D frames), graphical elements, measurement graphics of the displayed images, user-selectable elements, user settings, and other information (e.g., administrative information, personal information of the patient, and the like).

In addition to the image-processing module, the system controller 116 may also include one or more of a graphics module, an initialization module, a tracking module, and an analysis module. The image-processing module, the graphics module, the initialization module, the tracking module, and/or the analysis module may coordinate with one another to present information to the operator during and/or after the imaging session. For example, the image-processing module may be configured to display an acquired image on the display device 118, and the graphics module may be configured to display designated graphics along with the displayed image, such as selectable icons (e.g., image rotation icons) and measurement parameters (e.g., data) relating to the image. The controller may include algorithms stored within a memory of the controller for automatically adjusting a steering angle of an ultrasound signal, or beam, emitted by the elements 104 of the probe 106 and then generating an ultrasound image depicting at least a portion of a needle inserted in a body of a subject, as described further below with reference to FIGS. 2-4. The algorithms may further include image transforms and other routines for post-processing of the generated ultrasound images, as described further below with reference to FIGS. 5-7.

The screen of a display area 117 of the display device 118 is made up of a series of pixels which display the data acquired with the probe 106. The acquired data includes one or more imaging parameters calculated for each pixel, or group of pixels (for example, a group of pixels assigned the same parameter value), of the display, where the one or more calculated image parameters includes one or more of an intensity, velocity (e.g., blood flow velocity), color flow velocity, texture, graininess, contractility, deformation, and rate of deformation value. The series of pixels then make up the displayed image and/or Doppler spectrum generated from the acquired ultrasound data.

The system 100 may be a medical ultrasound system used to acquire imaging data of a scanned object (e.g., biological tissue including an inserted needle). The acquired image data may be used to generate one or more ultrasound images which may then be displayed via the display device 118 of the user interface 122. The one or more generated ultrasound images may include one or more 2D frames, for example. Specifically, the image-processing module discussed above may be programmed to generate and display the one or more 2D frames.

In general, ultrasound probes may be adjusted at a user interface via control of a steering angle of an emitted ultrasound beam. In some examples, the ultrasound probe may be utilized to image an object that is linear in at least one dimension, such as a needle. In such examples, for optimal imaging, it may desirable for the ultrasound beam to meet the object at a 90° angle with respect to the linear dimension. However, achieving this angle may be difficult via user control of a non-intuitive parameter such as the steering angle of the ultrasound beam. In some examples, such inherent difficulties may result in suboptimal visualization of the object.

According to embodiments disclosed herein, the above-described issues may be at least partly addressed by automatically adjusting the steering angle of the ultrasound beam and imaging an object (e.g., a needle) therefrom. At the user interface, a user may provide a target region where the object is expected to be. Thereafter, an angle may be determined between lines respectively parallel to the linear dimension of the object and a surface of the ultrasound probe. In some examples, the target region may be a target path of a needle, such that the angle may be an angle between a determined path of the needle and the surface of the ultrasound probe. The steering angle may then be adjusted towards the determined angle. In this way, the user may be provided with a more intuitive interface, allowing for more accurate visualization of the needle.

Referring now to FIG. 2, a method 200 is depicted for adjusting a steering angle of an ultrasound beam emitted by an ultrasound probe. Thereafter, imaging data may be received from the ultrasound probe, from which an image may be generated and displayed to a user at a display device.

Method 200 is described below with regard to the systems and components depicted in FIG. 1, though it should be appreciated that method 200 may be implemented with other systems and components without departing from the scope of the present disclosure. In some embodiments, method 200 may be implemented as executable instructions in any appropriate combination of the imaging system 100, an edge device (e.g., an external computing device) connected to the imaging system 100, a cloud in communication with the imaging system, and so on. As one example, method 200 may be implemented in non-transitory memory of a computing device, such as the controller (e.g., processor) of the imaging system 100 in FIG. 1.

Method 200 may begin at 205 where an ultrasound scan may be initiated. The ultrasound scan may include the ultrasound beam being emitted from transducer elements (e.g., 104) of an ultrasound probe (e.g., 106). The ultrasound beam may be directed toward a body of a subject, such as a patient. Therein, a needle, such as a biopsy needle, may be inserted, such that the ultrasound probe may image the object by collecting echoes reflected from an interaction of the ultrasound beam with the object. It will be appreciated by those skilled in the art that any object inserted in the body may be accordingly imaged in this way, and that method 200 should not be understood as being limited to a needle.

At 210, method 200 may include receiving a target region of the needle. The target region may be provided at a user interface (e.g., 122) of an ultrasound imaging system (e.g., 100). In some examples, the target region may be initialized by default in a center of a display area (e.g., 117) of a display device (e.g., 118). The display area may include an image depicting the body of the subject, as imaged from a previous ultrasound scan. In additional or alternative examples, a user may move or initialize the target region via a user selection. The user selection may include one or more of a touch selection, a navigation request, or a voice command. In some examples, and as will further be described below with reference to FIGS. 8 and 9, the touch selection may include "draggable" selection areas on the display device, such that the user may place a finger on one of the selection areas and move the selection area via touch control. In such examples, a sterile cover may be provided over a surface of the display device. In additional or alternative examples, the navigation request may include user-actuatable icons for moving the target region up, down, left, or right. In additional or alternative examples, the voice command may include recognition of navigation commands, such as "up," "down," "left," or "right." Further, the voice command may include a shorthand location request recognizable by an algorithm implemented in memory of the controller, such as "skin surface," "puncture point," etc. The target region may be a structure superimposed on the display area of the display device and represented by 2D coordinates, such as a linear target path (e.g., a line segment), a region around the target path (e.g., an oval), or a target area around a central point (e.g., a circle).

At 215, method 200 may include determining, or estimating, a path of the needle based on the target region of the needle. In examples wherein the target region includes a target path, the path of the needle may be projected along the target path such that the path of the needle may be a line including the target path. In examples wherein the target region includes a target area, one or more of a puncture point, an origin direction, and a penetration depth of the needle may be determined. In one example, position sensors of an exterior end of the needle (e.g., an end of the needle which is not inserted into the subject) may be communicatively coupled to the ultrasound imaging system such that a puncture point or an origin direction may be provided or inferred. The puncture point may include a location where the needle punctures skin of the subject. Further, the origin direction may include an orientation of the needle with respect to a reference plane of the position sensor. The penetration depth may be a depth that an interior end of the needle (e.g., an end of the needle which is inserted into the subject) is inserted into the subject. The penetration depth may be determined based on one or more of a center of the target area, the puncture point, and the origin direction. In other examples, one or more of the puncture point, the origin direction, and/or the penetration depth may be provided by the user at the user interface (e.g., 122). The path of the needle may then be projected based on one or more of the target area, the puncture point, the penetration depth, and the origin direction. As an example, the path of the needle may be projected along a line segment between the center of the target area and the puncture point. As another example, the path of the needle may be projected along a hypotenuse of a right triangle defined by the origin direction of the needle and the penetration depth (wherein a length of one side adjacent to a right angle of the right triangle may be the penetration depth, and wherein the origin direction may be used to determine an angle between the needle and a surface of the skin of the subject).

At 220, method 200 may include determining a needle angle based on the path of the needle and a position of the ultrasound probe (e.g., 106). The position of the ultrasound probe may be used to determine a line parallel to a surface of the ultrasound probe including the transducer elements (e.g., 104). For example, a position and an orientation of the ultrasound probe may be received from one or more position sensors therein. The surface of the ultrasound probe may then be inferred and located based on the received position and orientation of the ultrasound probe. That is, since the ultrasound probe may be manufactured to a set standard, the surface of the ultrasound probe may be determined relative to a reference position and a reference orientation of the one or more position sensors included in the ultrasound probe. The line parallel to the surface of the ultrasound probe and the path of the needle (e.g., a line parallel to a shaft of the needle) may then be used to define the needle angle. In some examples, the needle angle may be wider than an angle between the surface of the ultrasound probe and the path of the needle by a predefined amount, such that user error may be accounted for. For example, the user may have a general impression of where the needle is located in the body of the subject, but may not know a position of the needle precisely, resulting in small inaccuracies due to such user error.

As shown and described below with reference to FIG. 4, when a steering angle an ultrasound beam emitted by the ultrasound probe (e.g., 106) is equal to the needle angle, the ultrasound beam may be perpendicular to the path of the needle, providing optimal imaging of the needle. As such, at 225, method 200 may include determining whether a steering angle of an ultrasound beam emitted by the ultrasound probe (e.g., 106) is within a threshold angle (e.g., less than 20°, 15°, 10°, or 5°) of the needle angle. The steering angle may be defined by a line perpendicular to the surface of the ultrasound probe and a line parallel to the ultrasound beam.

If the steering angle is outside of the threshold angle of the needle angle, method 200 may proceed to 230 to adjust the steering angle toward the needle angle. In some examples, adjusting the steering angle toward the needle angle may include adjusting the steering angle to be within the threshold angle of the needle angle. In additional or alternative examples, adjusting the steering angle toward the needle angle may include matching the steering angle to the needle angle.

Once the steering angle has been adjusted toward the needle angle, or if the steering angle is determined at 225 to be within the threshold angle of the needle angle, method 200 may proceed to 235 to receive first imaging data from the ultrasound probe (e.g., 106). The first imaging data may include ultrasound echoes of the ultrasound beam emitted by the transducer elements (e.g., 104) of the ultrasound probe. In some examples, the first imaging data may further include physiological and/or temporal parameters, sets of 2D or 3D spatial coordinates, and other information useful for processing the first imaging data at an image processing module.

At 240, method 200 may include generating a first image depicting at least a portion of the needle inserted in the body of the subject from the imaging data. The first image may include a 2D frame corresponding to a targeted slice of received volumetric ultrasound data, for example. In some examples, second imaging data may be received from the ultrasound probe (e.g., 106) prior to insertion of the needle in the body of the subject. In such examples, a second image may be generated based on the second imaging data, wherein the second image may include a second 2D frame depicting the body of the subject without the needle. In this way, a difference between the first image and the second image may correspond to the needle and physiological changes in the body of the subject therefrom. The first image may thus be generated, in some examples, from both the first imaging data and the second image.

As an example, a so-called "dead zone" may be present in the first imaging data corresponding to a region not imaged by the ultrasound probe. However, the same region may be present in the second imaging data, allowing the region to be imaged in the second image and thereby the first image (e.g., by stitching together the first image from the first imaging data and the second image). Additionally, and as described below with reference to FIG. 7, since a further portion of the needle may be present in the "dead zone," the further portion may be projected based on a known length of the needle and thereby generated in the first image in the "dead zone."

As another example, an image transform may be executed on the target region in the first image. As described with reference to FIG. 5, the image transform may be a Radon transform, used to detect a linear structure representing the needle and to remove one or more artifacts from the target region (e.g., from bumping the ultrasound probe or moving the needle during imaging). Further, and as described below with reference to FIG. 6, a color or a brightness of the detected linear structure may be altered so as to depict the needle in higher contrast relative to the body of the subject.

At 245, method 200 may include displaying the first image at the display device (e.g., 118). The user of the display device may be presented with one or more functionalities for further manipulating the first image (e.g., zooming in, moving to different regions of the first image, defining a new target region for imaging, etc.). Two examples of such displays are provided hereinbelow with reference to FIGS. 8 and 9. In this way, a needle may be clearly imaged based on a user-supplied target region. A more intuitive user control may therefore by employed in needle imaging relative to control of another parameter such as the steering angle itself.

At 250, method 200 may determine whether a nerve, or other physiological feature, has been identified within a threshold distance (e.g., 2 mm, 1 mm, 0.5 mm, 0.1 mm) of the target region. In some examples, a nerve recognition algorithm may be implemented in memory of the controller so as to prevent a needle from reaching an identified nerve or to alert the user of a presence of the identified nerve. As such, if the nerve is identified within the threshold distance of the target region, method 200 may proceed to 255 to generate and display a notification or an alert. The notification may indicate to the user of the ultrasound imaging system (e.g., 100) that the path of the needle (as determined from the target region, for example) is within the threshold distance of the identified nerve. In some examples, the notification may include a prompt indicating that the needle should be retracted or re-inserted in a region away from the identified nerve. In additional or alternative examples, the notification may request user confirmation of the identified nerve. Method 200 may then end.

If no nerve is identified within the threshold distance of the target region, method 200 may proceed to 260 to maintain a current display. For example, the current display may include the image as generated and displayed as described hereinabove. Method 200 may then end.

Referring now to FIG. 3, a method 300 is depicted for adjusting the steering angle of the ultrasound beam emitted by the ultrasound probe in response to a position of the ultrasound probe being altered, and then imaging at least a portion of a needle therefrom. In some examples, method 300 may follow method 200. As such, in some examples, an image depicting at least the portion of the needle may initially be generated and displayed to a user.

Method 300 is described below with regard to the systems and components depicted in FIG. 1, though it should be appreciated that method 300 may be implemented with other systems and components without departing from the scope of the present disclosure. In some embodiments, method 300 may be implemented as executable instructions in any appropriate combination of the imaging system 100, an edge device (e.g., an external computing device) connected to the imaging system 100, a cloud in communication with the imaging system, and so on. As one example, method 300 may be implemented in non-transitory memory of a computing device, such as the controller (e.g., processor) of the imaging system 100 in FIG. 1.

Method 300 may begin at 305, where method 300 may include receiving the position of the ultrasound probe (e.g., 106). The position of the ultrasound probe may be received from one or more position sensors therein. In some examples, receiving the position of the ultrasound probe may follow receiving one or more previous positions of the ultrasound probe. As such, at 310, method 300 may include determining whether the position of the ultrasound probe has been altered (e.g., relative to the one or more previous positions). If the position of the ultrasound probe has not been altered, method 300 may proceed to 315 to maintain a current display. For example, the current display may include the image as generated and displayed according to method 200, as described above with reference to FIG. 2. Method 300 may then end.

If the position of the ultrasound probe (e.g., 106) has been altered, method 300 may proceed to 320 to determine whether the altered position of the ultrasound probe is outside of a detection range of the needle. For example, the position of the ultrasound probe may have been manually adjusted away from the target region (e.g., where the needle is assumed to be) or from where the needle has been previously imaged and detected via the image transform. As such, the needle may be subsequently determined to no longer be present in imaging data received from the ultrasound probe in the altered position. Thus, if the altered position of the ultrasound probe is outside of the detection range, method 300 may proceed to 325 to generate and display a notification or an alert. The notification may indicate to the user of the ultrasound imaging system (e.g., 100) that the ultrasound probe is outside of the detection range of the needle. In some examples, the notification may include a prompt indicating that the altered position of the ultrasound probe should be manually adjusted to back within the detection range of the needle. Further, in some examples, the image may continue to be displayed and may change in appearance in response to newly received imaging data (e.g., in response to the ultrasound probe being moved). Method 300 may then end.

If the altered position of the ultrasound probe is within the detection range, method 300 may proceed to 330 to adjust the steering angle of the ultrasound beam emitted by the transducer elements (e.g., 104) of the ultrasound probe (e.g., 106) based on the target region of the needle and the altered position of the ultrasound probe. In some examples, an analogous procedure to that described at 220 to 230 of method 200 as described with reference to FIG. 2 may be employed to adjust the steering angle toward the needle angle. For example, at 335, an updated needle angle may be determined based on the target region of the needle and the altered position of the ultrasound probe. Then, at 340, the steering angle may be adjusted towards the updated needle angle.

At 345, method 300 may include receiving updated imaging data from the ultrasound probe (e.g., 106). The updated imaging data may include ultrasound echoes of the ultrasound beam emitted by the transducer elements (e.g., 104) of the ultrasound probe. In some examples, the updated imaging data may further include physiological and/or temporal parameters, sets of 2D or 3D spatial coordinates, and other information useful for processing the updated imaging data at the image processing module.

At 350, method 300 may include generating an updated image depicting at least a portion of the needle inserted in the body of the subject from the updated imaging data. The updated image may include a 2D frame corresponding to a targeted slice of received volumetric ultrasound data, for example. Post-processing of the updated imaging data, such as via an image transform, may include one or more of the examples described at 240 of method 200 as described with reference to FIG. 2.

In some examples, the image transform may be utilized to identify the needle depicted in the image and store a location thereof. Thus, when the position of the ultrasound probe has been altered and the needle is subsequently re-imaged, the location of the needle in the image may be updated, such that the needle may be tracked by the ultrasound imaging system (e.g., 100) provided herein. In one example, the nerve recognition algorithm described above with reference to FIG. 2 may further detect whether a position of the needle itself is within a threshold distance of an identified nerve. If so, a notification may be generated, analogous to the notification generated at 255 of method 200 as described above with reference to FIG. 2. If not, a current display may be maintained.

At 355, method 300 may include displaying the updated image at the display device (e.g., 118). The user of the display device may be presented with one or more functionalities for further manipulating the updated image (e.g., zooming in, moving to different regions of the updated image, defining a new target region for imaging, etc.). Two examples of such displays are provided hereinbelow with reference to FIGS. 8 and 9. In this way, the image displayed to the user at the display device may be automatically updated when the position of the ultrasound probe is altered. Method 300 may then end.

Referring now to FIG. 4, a schematic diagram 400 depicts geometric considerations of adjusting a steering angle 420 of one or more ultrasound beams 406 emitted by the transducer elements 104 of the ultrasound probe 106. Such geometric considerations may be employed by the ultrasound imaging system as described with reference to FIG. 1 and the methods described with reference to FIGS. 2 and 3. Specifically, the ultrasound beam(s) 406 may be directed toward a needle 402 inserted in a body 404 of a subject. The ultrasound beam(s) 406 may reflect off of a portion of the needle 402, such that the portion of the needle 402 may be imaged by processing echoes of the ultrasound beam(s) 406 received at a surface 104a of the transducer elements 104.

A needle path 408 may be defined parallel to a shaft of the needle 402, and a first line 410 may be defined parallel to the surface 104a of the transducer elements 104 of the ultrasound probe 106. At an intersection of the needle path 408 and the first line 410, a needle angle 412 may be defined. Further, a second line 414 may be defined parallel to the ultrasound beam(s) 406, and a third line 416 may be defined perpendicular to the first line 410 (e.g., such that an angle 418 defined between the first line 410 and the third line 416 is 90°). At an intersection of the second line 414 and the third line 416, the steering angle 420 may be defined. Further, at an intersection of the needle path 408 and the second line 414, an angle 422 may be defined.

For optimal imaging of the needle 402, the angle 422 should be as close as possible to 90°. Geometrically, to obtain a value of 90°, the needle angle 412 and the steering angle 420 must be equal. The needle angle 412 may be determined by $$\arctan\left(\frac{P_{2,Y} - P_{1,Y}}{P_{2,X} - P_{1,X}}\right)$$

where a first point $P_1$ and a second point $P_2$ are located along the needle path 408, and X and Y coordinates are defined with respect to axes parallel to first line 410 and third line 416, respectively, such that $P_{1,X}$ and $P_{2,X}$ refer to X components of $P_1$ and $P_2$, respectively, and $P_{1,Y}$ and $P_{2,Y}$ refer to Y components of $P_1$ and $P_2$, respectively. The steering angle 420 may then be adjusted to match the needle angle 412. In this way, the ultrasound beam may be set to be perpendicular to the needle by adjusting the steering angle to equal the angle between the surface of the ultrasound probe and the path of the needle.

Referring now to FIG. 5, a schematic diagram 500 depicts a first example of an image transform 550 for an image 502 depicting a portion of a needle 504 in a target region 506. In some examples, the image 502 may be imaged by an ultrasound imaging system, such as the ultrasound imaging system as described with reference to FIG. 1, implementing a method for generating an image, such as in the methods described with reference to FIGS. 2 and 3. As shown, one or more artifacts 508 may be present in the target region 506 surrounding the needle 504. In some examples, the one or more artifacts 508 may result from bumping the ultrasound probe (e.g., 106) or moving the needle 504 during imaging. The image transform 550 may be a transform, such as a Radon transform, operable to detect linear structures in a 2D image. In some examples, each of the needle 504 and the one or more artifacts 508 may be identifiable by the image transform 550. Further, the image transform 550 may distinguish the needle 504 as more well-defined and/or brighter than the one or more artifacts 508. As such, the image transform 550 may generate an image 552 with the one or more artifacts 508 removed.

Referring now to FIG. 6, a schematic diagram 600 depicts a second example of an image transform 650 for an image 602 depicting a portion of a needle 604 in a target region 606. In some examples, the image 602 may be imaged by an ultrasound imaging system, such as the ultrasound imaging system as described with reference to FIG. 1, implementing a method for generating an image, such as in the methods described with reference to FIGS. 2 and 3. As shown, the needle 604 may appear as a dark color, such that the needle 604 may be difficult to distinguish from other structures depicted in the image 602. The image transform 650 may be a transform, such as a Radon transform, operable to detect linear structures in a 2D image. In some examples, the needle 604 may be identifiable by the image transform 650. The image transform 650 may be further operable to alter the color or brightness of the needle 604. As such, the image transform 650 may generate an image 652 wherein a needle 654 is depicted in a brighter color, or with increased brightness, as compared to the needle 604 depicted by the image 602.

Referring now to FIG. 7, a schematic diagram 700 depicts an example process 750 for generating a portion 754 of a needle 704. In some examples, the image 702 may be imaged by an ultrasound imaging system, such as the ultrasound imaging system as described with reference to FIG. 1, implementing a method for generating an image, such as in the methods described with reference to FIGS. 2 and 3. As shown, a dead zone 706 corresponding to a region not imaged by the ultrasound probe (e.g., 106) may be present in the image 702. In the depicted example, the portion 754 of the needle 704 is not present in the image 702. However, the example process 750 may project the portion 754 based on a known length of the needle 704, and thereby generate the portion 754 in the image 752.

Referring now to FIG. 8, a first example user interface display 800 of a display device 802 is depicted. In one example, the display device 802 may be the display device 118 shown in FIG. 1. The first example user interface display 800 may include an image 804 generated from ultrasound imaging data received by the ultrasound probe (e.g., 106). A dead zone 806 corresponding to a region not imaged by the ultrasound probe may be present in the image 804. At the display device 802, a user may define a target region 810 where the user expects a needle to be imaged. As shown, the target region 810 may include multiple selection areas (e.g., first selection area 812 and second selection area 814) which may be moved (e.g., "dragged and dropped") by the user via touch, a mouse, a keyboard, etc. Alternatively, a user-actuatable icon 820 may be operable to move the target region 810 up, down, left, and right. As shown, the target region 810 may at least partially include a region outside of the image 804. In this way, a user may manipulate a target region at a display device to provide a prediction of where a needle will be imaged.

Referring now to FIG. 9, a second example user interface display 900 of a display device 902 is depicted. In one example, the display device 902 may be the display device 118 shown in FIG. 1. The second example user interface display 900 may include an image 904 generated from ultrasound imaging data received by the ultrasound probe (e.g., 106). A dead zone 906 corresponding to a region not imaged by the ultrasound probe may be present in the image 904. As shown, a needle 908 may be imaged in a target region 910. The target region 910 may have been defined by a user prior to imaging the needle 908, as described above with reference to FIG. 8. As shown, the target region 910 may include multiple selection areas (e.g., first selection area 912 and second selection area 914) which may be moved (e.g., "dragged and dropped") by the user via touch, a mouse, a keyboard, etc. for further imaging. Alternatively, a user-actuatable icon 920 may be operable to move the target region 910 up, down, left, and right. As shown, the target region 910 may at least partially include a region outside of the image 904. In this way, a user may manipulate a target region at a display device for further imaging of a needle even after having imaged the needle.

In this way, a user may supply a target region of a needle, from which a steering angle of an ultrasound beam may be automatically adjusted. In one example, an image depicting the needle may be subsequently generated via an ultrasound imaging system, and displayed to the user on a display device. A technical effect of adjusting the steering angle based on the user-supplied target region is that a more intuitive user interface is provided for the user, as geometric calculations are performed by a controller of the ultrasound imaging system. In some examples, one or more image transforms may be implemented in memory of the controller to further refine the generated image of the needle. The technical effect of utilizing such image transforms is that artifacts may be removed from a vicinity of the depicted needle and/or a color of the depicted needle may be altered or brightened.

In one embodiment, a method comprises receiving a target path or a target area of a needle, and adjusting a steering angle of an ultrasound beam emitted from an ultrasound probe based on the target path or the target area. In a first example of the method, adjusting the steering angle of the ultrasound beam based on the target path or the target area includes locating a surface of the ultrasound probe, inferring a path of the needle based on the target path or the target area, determining a needle angle between the path of the needle and the surface of the ultrasound probe, and responsive to determining that the steering angle does not match the needle angle within a threshold, adjusting the steering angle toward the needle angle. In a second example of the method, optionally including the first example, responsive to receiving the target area of the needle, inferring the path of the needle based on the target area includes determining a puncture point of the needle, and projecting the path of the needle between a center of the target area and the puncture point. In a third example of the method, optionally including one or more of the first and second examples, responsive to receiving the target path of the needle, inferring the path of the needle based on the target path includes projecting the path of the needle along the target path. In a fourth example of the method, optionally including one or more of the first through third examples, locating the surface of the ultrasound probe includes receiving a position and an orientation of the ultrasound probe, and locating the surface of the ultrasound probe based on the position and the orientation of ultrasound probe. In a fifth example of the method, optionally including one or more of the first through fourth examples, determining that the steering angle does not match the needle angle includes the steering angle being outside of a threshold angle of the needle angle.

In another embodiment, a system comprises an ultrasound probe, a user interface configured to receive input from a user of the system, a display device, and a processor configured with instructions in non-transitory memory that when executed cause the processor to receive, at the user interface, a user selection, estimate a path of a needle based on the user selection, adjust a steering angle of an ultrasound beam of the ultrasound probe based on a position of the ultrasound probe and the path of the needle, receive first imaging data from the ultrasound probe, generate a first image based on the first imaging data, the first image depicting at least a portion of the needle inserted in a body, and display, at the display device, the first image. In a first example of the system, the user selection includes a target region for the path of the needle. In a second example of the system, optionally including the first example, estimating the path of the needle based on the user selection includes determining an origin direction of the needle, determining a penetration depth of the needle based on the target region, and projecting the path of the needle based on the penetration depth and the origin direction. In a third example of the system, optionally including one or more of the first and second examples, generating the first image based on the first imaging data includes receiving second imaging data from the ultrasound probe prior to insertion of the needle in the body, generating a second image based on the second imaging data, and generating the first image based on the first imaging data and the second image. In a fourth example of the system, optionally including one or more of the first through third examples, generating the first image based on the first imaging data and the second image includes generating a further portion of the needle in the first image in a region where the needle is not shown in the first imaging data. In a fifth example of the system, optionally including one or more of the first through fourth examples, generating the first image based on the first imaging data and the second image includes executing an image transform on the target region in the first image. In a sixth example of the system, optionally including one or more of the first through fifth examples, executing the image transform includes removing one or more artifacts from the target region. In a seventh example of the system, optionally including one or more of the first through sixth examples, executing the image transform includes altering a color or a brightness of the needle in the target region. In an eighth example of the system, optionally including one or more of the first through seventh examples, the user selection comprises one or more of a touch screen selection, a navigation request, or a voice command.

In yet another embodiment, a method comprises determining a path of a needle, performing a first adjustment of a steering angle of an ultrasound beam of an ultrasound probe based on a position of the ultrasound probe and the path of the needle, receiving imaging data from the ultrasound probe, generating an image based on the imaging data, the image including at least a portion of the needle inserted in a body, displaying, at a display device, the image, and responsive to the position of the ultrasound probe being altered performing a second adjustment of the steering angle based on the altered position of the ultrasound probe and the path of the needle, receiving updated imaging data from the ultrasound probe, updating the image based on the updated imaging data, and displaying, at the display device, the updated image. In a first example of the method, the method further comprises, responsive to a nerve being identified within a threshold distance of the path of the needle, generating and displaying a notification at the display device. In a second example of the method, optionally including the first example, the notification indicates that the path of the needle is within the threshold distance of the identified nerve. In a third example of the method, optionally including one or more of the first and second examples, the notification requests user confirmation of the identified nerve. In a fourth example of the method, optionally including one or more of the first through third examples, the method further comprises, responsive to the altered position of the ultrasound probe being outside a detection range of the path of the needle, generating and displaying a notification at the display device.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:
   an ultrasound probe;
   a user interface configured to receive input from a user of the system;
   a display device; and
   a processor configured with instructions in non-transitory memory that when executed cause the processor to:
      display, at the display device via the user interface, a target region of a needle, the target region indicating an elongated area on an ultrasound image of a subject where the needle is expected to be imaged, the target region including exactly two, non-overlapping selection areas;
      receive, at the user interface, a user selection to move the target region, wherein the user selection to move the target region comprises the moving of at least one selection area of the two non-overlapping selection areas of the target region;
      estimate a path of the needle based on the target region;
      adjust a steering angle of an ultrasound beam of the ultrasound probe based on a position of the ultrasound probe and the path of the needle;
      receive first imaging data from the ultrasound probe;
      generate a first image based on the first imaging data, the first image depicting at least a portion of the needle inserted in a body;
      display, at the display device, the first image; and
      responsive to a nerve being identified within a threshold distance of the path of the needle, generating and displaying a notification at the display device, wherein the notification indicates that the path of the needle is within the threshold distance of the identified nerve or requests user confirmation of the identified nerve.

2. The system of claim 1, wherein estimating the path of the needle includes:
   determining an origin direction of the needle;
   determining a penetration depth of the needle based on the target region; and
   projecting the path of the needle based on the penetration depth and the origin direction.

3. The system of claim 1, wherein the user selection comprises one or more of a touch screen selection, a navigation request, and a voice command, wherein displaying the target region comprises displaying the target region at a default position in a center of a display area of the display device, wherein the target region is moved from the default position to a desired position responsive to the user selection, wherein determining the projected path of the needle based on the target region comprises determining the projected path of the needle based on the target region at the desired position, and wherein generating the first image based on the first imaging data includes:
   receiving second imaging data from the ultrasound probe prior to insertion of the needle in the body;
   generating a second image based on the second imaging data; and
   generating the first image based on the first imaging data and the second image.

4. The system of claim 3, wherein generating the first image based on the first imaging data and the second image includes:
   generating a further portion of the needle in the first image in a region where the needle is not shown in the first imaging data.

5. The system of claim 3, wherein generating the first image based on the first imaging data and the second image includes:
   executing an image transform on the target region in the first image, including one or more of removing one or more artifacts from the target region and altering a color or a brightness of the needle in the target region.

6. A method, comprising:
   displaying, on a display device, a target region of a needle, the target region indicating an elongated area on an ultrasound image of a subject where the needle is expected to be imaged, the target region including exactly two, non-overlapping selection areas;
   receiving a user selection to move the target region, wherein the user selection to move the target region comprises the moving of at least one selection area of the two non-overlapping selection areas of the target region;
   determining a projected path of the needle based on the target region;
   performing a first adjustment of a steering angle of an ultrasound beam of the ultrasound probe based on the position of the ultrasound probe and the projected path of the needle, including determining a surface of the ultrasound probe, determining an angle of the needle between the projected path of the needle and the surface of the ultrasound probe, and adjusting the steering angle of the ultrasound beam to be within a threshold angle of the angle of the needle;
   receiving imaging data from the ultrasound probe;
   generating an image based on the imaging data, the image including at least a portion of the needle inserted in a body, wherein the at least the portion of the needle is shown with an increased brightness;
   displaying, at a display device, the image; and
   responsive to the position of the ultrasound probe being altered:
      performing a second adjustment of the steering angle based on the altered position of the ultrasound probe and the projected path of the needle;
      receiving updated imaging data from the ultrasound probe;
      updating the image based on the updated imaging data; and
      displaying, at the display device, the updated image;
   responsive to a nerve being identified within a threshold distance of the projected path of the needle, generating and displaying a notification at the display device, wherein the notification indicates that the projected path of the needle is within the threshold distance of the identified nerve or requests user confirmation of the identified nerve.

7. The method of claim 6, wherein receiving the user selection includes receiving a drag and drop input to the at least one selection area, and further comprising receiving a second user input to move the target region while the image is displayed.

8. The method of claim 6, wherein displaying the target region comprises displaying the target region at a default position in a center of a display area of the display device, wherein the target region is moved from the default position to a desired position responsive to the user selection, and wherein determining the projected path of the needle based on the target region comprises determining the projected path of the needle based on the target region at the desired position.

9. The method of claim 6, further comprising:
responsive to the altered position of the ultrasound probe being outside a detection range of the projected path of the needle, generating and displaying a notification at the display device.

10. The method of claim 6, wherein receiving the user selection comprises receiving one or more of a touch selection, a navigation request, and a voice command via a user interface, and wherein receiving imaging data from the ultrasound probe is in response to adjusting the steering angle of the ultrasound beam to be within the threshold angle of the angle of the needle.

11. The method of claim 6, wherein the target region includes a target path and wherein determining the projected path of the needle based on the target region comprises:
projecting a path of the needle along the target path such that the projected path of the needle is a line including the target path.

12. The method of claim 6, wherein determining the surface of the ultrasound probe comprises:
determining the surface of the ultrasound probe relative to a reference position and a reference orientation of one or more position sensors included in the ultrasound probe.

13. The method of claim 6, wherein performing the second adjustment of the steering angle based on the altered position of the ultrasound probe and the projected path of the needle comprises:
determining an updated angle of the needle based on the projected path of the needle and the surface of the ultrasound probe in the altered position; and
adjusting the steering angle of the ultrasound beam to be within the threshold angle of the updated angle of the needle.

14. The method of claim 6, wherein the elongated area is a rectangle extending from an edge of the image.

15. The method of claim 6, wherein the ultrasound image is displayed on the display device with the target region superimposed on the ultrasound image, and wherein the target region extends beyond the ultrasound image with at least one of the two non-overlapping selection areas being outside of the ultrasound image.

16. The method of claim 6, wherein the two non-overlapping selection areas comprise a first selection area at a first terminating end of the target region and a second selection area at a second terminating end of the target region.

17. The method of claim 16, wherein said receiving the user selection to move the target region comprises moving the first selection area in response to a first touch input via a touch-sensitive display or a touchpad and/or moving the second selection area in response to a second touch input via the touch-sensitive display or the touchpad, and wherein the target region extends from the first selection area to the second selection area.

18. The method of claim 6, further comprising detecting the needle in the image and removing one or more artifacts from the target region once the needle has been detected, wherein the target region continues to be displayed as the needle is imaged.

* * * * *